United States Patent [19]

Rodewald

[11] Patent Number: 4,751,341
[45] Date of Patent: Jun. 14, 1988

[54] OLIGOMERIZATION OF OLEFINS WITH BF₃ TREATED ZEOLITE

[75] Inventor: Paul G. Rodewald, Rocky Hill, N.J.

[73] Assignee: Mobil Oil Corporation, New York, N.Y.

[21] Appl. No.: 97,374

[22] Filed: Sep. 16, 1987

Related U.S. Application Data

[63] Continuation of Ser. No. 860,371, May 6, 1986, abandoned, which is a continuation of Ser. No. 787,943, Oct. 16, 1985, abandoned, which is a continuation-in-part of Ser. No. 701,313, Feb. 13, 1985, Pat. No. 4,567,310, which is a continuation-in-part of Ser. No. 526,764, Aug. 26, 1983, abandoned, which is a continuation of Ser. No. 355,419, Mar. 8, 1982, abandoned.

[51] Int. Cl.⁴ .................................................. C07C 2/02
[52] U.S. Cl. .................................... 585/533; 585/722; 585/726
[58] Field of Search ......................................... 585/533

[56] References Cited

U.S. PATENT DOCUMENTS

| | | | |
|---|---|---|---|
| 3,756,942 | 9/1923 | Chattanach | 208/137 |
| 3,928,483 | 12/1975 | Chang et al. | 208/135 |
| 4,029,716 | 6/1977 | Kaeding | 585/407 |
| 4,324,940 | 4/1982 | Dessau | 585/466 |
| 4,427,786 | 1/1984 | Miale et al. | 502/61 |
| 4,512,876 | 4/1985 | Miale et al. | 208/114 |
| 4,540,840 | 9/1985 | Miale et al. | 585/640 |

*Primary Examiner*—Olik Chaudhuri
*Attorney, Agent, or Firm*—Alexander J. McKillop; Michael G. Gilman; Dennis P. Santini

[57] ABSTRACT

A modified ZSM-5 type zeolite is provided by treatment of a ZSM-5 type zeolite with BF₃. The novel product is characterized by reduced pore size and enhanced shape-selectivity, or by enhanced activity, or by both. This invention also provides a process for catalytically converting organic compounds by use of the novel composition, an illustrative conversion being the catalytic conversion of methanol to hydrocarbons and $C_2$-$C_7$ olefins to gasoline components.

17 Claims, No Drawings

OLIGOMERIZATION OF OLEFINS WITH BF3 TREATED ZEOLITE

CROSS-REFERENCE TO RELATED APPLICATIONS

This is a continuation of copending application Ser. No. 860,371, filed on May 6, 1986, now abandoned, which is a continuation of application Ser. No. 787,943, filed Oct. 16, 1985, now abandoned, which is a continuation-in-part of Ser. No. 701,313, filed Feb. 13, 1985, now U.S. Pat. No. 4,567,310, which is a continuation-in-part of Ser. No. 526,764, filed Aug. 26, 1983, now abandoned, which is a continuation of Ser. No. 355,419 filed Mar. 8, 1982, now abandoned.

BACKGROUND OF THE INVENTION

1. Field of the Invention

This invention is concerned with the catalytic conversion of hydrocarbons and other organic compounds over crystalline aluminosilicate zeolites of the ZSM-5 type which have been modified by treatment with $BF_3$, to provide enhanced selectivity, activity, or both, and with the method for preparing such catalysts.

2. Description of the Prior Art

Zeolitic materials, both natural and synthetic, have been demonstrated in the past to have catalytic properties for various types of conversions. One such conversion which has generated considerable interest is the production of hydrocarbons, including olefins and gasoline from alcohols and ethers.

U.S. Pat. No. 4,025,575 describes a process by which lower alcohols and/or their ethers are converted to a mixture of $C_2$-$C_5$ olefins by contact at subatmospheric inlet partial pressure with a crystalline aluminosilicate zeolite of the ZSM-5 type.

U.S. Pat. No. 3,931,349, issued Jan. 9, 1976, also discloses a process for the conversion of methanol to gasoline utilizing a ZSM-5 type catalyst.

U.S. Pat. No. 4,083,888, issued on Apr. 11, 1978, discloses a process for the manufacture of hydrocarbons by the catalytic conversion of methanol in the presence of a substantially anhydrous diluent and a ZSM-5 type zeolite.

There are many other patents and publications which describe the conversion of methanol to hydrocarbons, including gasoline, such as U.S. Pat. Nos. 3,931,349; 3,969,426; 3,899,544; 3,894,104; 3,904,916; and 3,894,102, the disclosures of which are incorporated herein by reference. Other conversions include, for example, propylene oligomerization, toluene disproportionation, xylene isomerization, alkylation of aromatics with alcohol or olefins, such as toluene+ethylene—p-ethyltoluene, and dewaxing, i.e., shape-selective cracking of wax molecules.

U.S. Pat. No. 4,163,028 discloses the isomerization of a feedstock containing xylene in the presence of ZSM-5. U.S. Pat. No. 4,268,420 describes a crystalline borosilicate AMS-1B (ZSM-5) which can be used as a catalyst in the isomerization of xylene.

U.S. Pat. No. 4,292,457 discloses the alkylation of aromatic hydrocarbons in the presence of a borosilicate AMS-1B (ZSM-5) catalyst. U.S. Pat. No. 4,269,813 discloses the use of this catalyst in disproportionation and transalkylation processes as well as in xylene isomerization. Similar processes in the presence of ZSM-4 and ZSM-5 catalysts are also disclosed in U.S. Pat. No. 4,377,502.

U.S. Pat. Nos. 4,208,305 and 4,238,318 disclose, in addition to the above catalytic processes, upgrading cracked gasoline and naphtha, preparation of olefins from alcohols, preparation of olefinic gasoline, alkylation of olefins, separation of hydrogen mixtures, and catalytic hydrodewaxing of hydrocarbon oils in the presence of zeolite catalysts.

All of the foregoing patents are incorporated herein by reference.

SUMMARY OF THE INVENTION

It has now been found that a ZSM-5 type zeolite is advantageously modified by contacting the zeolite with gaseous anhydrous boron trifluoride at moderately elevated temperature, such as 150° C., and for a relatively short time, such as 30 minutes, as more fully described hereinbelow. The product of this treatment exhibits reduced activity for cracking a refractory hydrocarbon such as normal hexane, as measured by the alpha test conducted at 538° C., and enhanced activity for the conversion of methanol to hydrocarbons, as more fully described hereinbelow. Furthermore, as will be shown by example, the novel modified zeolite catalysts in general show a much higher catalytic activity for conversions of less refractory feedstocks than normal hexane than would be expected from their alpha values. Such catalytic conversions of organic compounds include olefin oligomerization, toluene disproportionation, xylene isomerization, catalytic dewaxing, and the conversion of methanol to hydrocarbons, including olefins and/or gasoline.

The boron trifluoride treated zeolite catalyst makes it possible to use lower operating temperatures or, quite obviously, to use the same temperatures as generally employed in the prior art but at higher space velocities. It is immediately apparent that having a catalyst of enhanced activity has the potential for lowering operating costs due to the fact that lower temperatures can be used and allowing for a greater throughput due to the fact that higher space velocities can be employed.

The treatment with boron trifluoride by the method described also imparts changes in chemical composition and physical properties as well as catalytic properties. These are illustrated by Example 21. This example suggests that a reaction occurs between the zeolite and $BF_3$. It also demonstrates that the modified zeolites have somewhat smaller pores and therefore will favor formation of "thinner" molecules such as ethylene (in methanol conversion) and para-xylene (in xylene isomerization).

DESCRIPTION OF THE PREFERRED EMBODIMENTS

U.S. Pat. No. 4,567,310, issuing from application Ser. No. 701,313, is incorporated herein by reference in its entirety.

The novel catalyst of this invention is prepared simply by treating a ZSM-5 type zeolite at least partially in the acid form, preferably ZSM-5, with boron trifluoride. The treated zeolite preferably is purged to remove any excess $BF_3$ that may be present. The method of treatment is not narrowly critical and typical conditions utilize boron trifluoride flowing at 30 cc/min. through a 1 gram catalyst bed maintained at 150° C. However, it is noted that flow rates of 1 to 600 cc/min. through 1 gram of catalyst bed maintained at a temperature of from 25° to 500° C. are also operable to produce the enhanced catalyst of this invention. The time at which the boron trifluoride is contacted with the catalyst is also not narrowly critical and activation can be obtained at periods of time ranging from 0.01 hour to 10 hours and preferably from about 0.1 to 2.0 hours. Following treatment with boron trifluoride, the catalyst is ready for use, but it may be air calcined, if desired. Contacting with boron trifluoride is highly effective at atmospheric pressure, but subatmospheric or elevated pressure may be used.

The conversion of lower alcohols, their ethers, or mixtures therof to $C_2$-$C_5$ olefins and to heavier hydrocarbons and the conversion of methanol to olefins, to gasoline, and to other hydrocarbons with ZSM-5 type catalyst is well known. The conditions for these reactions are well documented in the patents incorporated herein by reference. The modified zeolites of this invention are advantageously used in these conversions. Other conversions in which the modified zeolites are advantageously used will now be described.

The feedstock to the present process may comprise $C_2$-$C_7$ paraffins and/or olefins of at least two carbon atoms. When the feedstock comprises paraffins, product comprises aromatics, e.g., benzene, toluene and xylenes, and conversion conditions include a temperature of from about 100° C. to about 700° C., a pressure of from about 10 kPa to about 11000 kPa, preferably from 10 kPa to 7000 kPa, a liquid hourly space velocity (LHSV) of from about 0.1 $hr^{-1}$ to about 500 $hr^{-1}$, preferably from 0.5 $hr^{-1}$ to 400 $hr^{-1}$, and a hydrogen/hydrocarbon mole ratio of from 0 (no added hydrogen) to about 20. Under these same conversion conditions, a feedstock comprising $C_2$-$C_7$ olefins is converted to product comprising aromatics, e.g., benzene, toluene and xylenes.

A feedstock to the present process may comprise primarily $C_2$-$C_7$ olefins for conversion to gasoline and distillate products when the conversion conditions are tailored to be within the following ranges. In general, the temperature will be maintained at from about 190° C. to about 375° C., the pressure at from about 400 kPa to about 11000 kPa, preferably from 400 kPa to about 7000 kPa, and the liquid hourly space velocity (LHSV based on feedstock olefin) at from about 0.3 to about 2, preferably from 0.5 to 2 $hr^{-1}$. Specifically when the present process is operated in the distillate mode, the temperature will be from about 190° C. to about 315° C., the pressure from about 4200 kPa to about 11000 kPa, preferably from 4200 kPa to 7000 kPa, and the LHSV from about 0.3 to about 1.0 $hr^{-1}$, preferably from 0.5 to 1.0 $hr^{-1}$. When the present process is operated in the gasoline mode, the temperature will be from about 230° C. to about 375° C., the pressure from about 400 kPa to about 4700 kPa, preferably from 400 kPa to 3000 kPa and the LHSV from about 0.3 to about 2.0, preferably from 0.5 to 2.0 $hr^{-1}$. The feedstocks, products, process conditions and other variables for conversion of olefins to higher hydrocarbons are detailed in U.S. Pat. No. 4,456,779, incorporated entirely herein by reference.

Such conversion processes also include, as a nonlimiting example, cracking hydrocarbons to lower molecular weight hydrocarbons with reaction conditions preferably including a temperature of from about 230° C. to about 800° C., a pressure of from about 0.1 atmosphere (bar) to about 35 atmospheres and a weight hourly space velocity of from about 0.1 $hr^{-1}$ to about 200 $hr^{-1}$, or a liquid hourly space velocity of from about 0.6 $hr^{-1}$ to about 10 $hr^{-1}$. When the feedstock to the present process comprises a heavy oil stock to be dewaxed, preferred conversion temperature is from about 230° C. to about 500° C. When the feedstock comprises a lubricating oil base stock to be dewaxed, preferred conversion temperature is also from about 230° C. to about 500° C.

Feedstock aromatic compounds may be converted hereby, and include individually and in mixture benzene and monocyclic alkyl-substituted benzene of from 7 to 10 carbon atoms having the structure

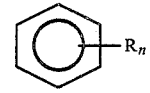

wherein R is methyl, ethyl or a combination thereof, and n is an integer of from 1 to 4. In other words, the feedstock aromatic compounds may be benzene, benzene containing from 1 to 4 methyl and/or ethyl group substituents, and mixtures thereof. Non-limiting examples of such feedstock compounds include benzene, toluene, xylene, ethylbenzene, mesitylene (1,3,5-trimethylbenzene), durene (1,2,4,5-tetramethylbenzene), pseudocumene (1,2,4-trimethylbenzene) and mixtures thereof.

Other reactant species may be present, such as for alkylation. Alkylating agent species include olefins such as ethylene, propylene, dodecylene, as well as formaldehyde, alkyl halides and alcohols; the alkyl portion thereof having from 1 to 24 carbon atoms. Numerous other acyclic compounds having at least one reactive alkyl radical may be utilized as alkylating agents.

Products of the process for conversion of aromatics include alkyl-substituted benzene compounds which differ from feedstock compounds depending upon the conversion desired. The following listing presents non-limiting examples:

| Feedstock Aromatic Compounds Include | Other Reactants Include | Product Aromatic Compounds Include |
| --- | --- | --- |
| Benzene | Ethylene | Ethylbenzene |
| Toluene | Methanol | Xylene isomers |
| Xylene isomers, e.g., 9:73:18 wt. ratio of para:meta:ortho | — | Different combination of xylene isomers, e.g. 23:57:20 wt. ratio of para:meta:ortho |
| Toluene | — | Benzene and xylenes |
| Benzene | Propylene | Cumene and diisopropylbenzene |
| Toluene | Propylene | Cymene isomers |

Mechanisms of the present process may be isomerization, alkylation, transalkylation and disproportionation. Disproportionation is a special case of transalkylation in which the alkylatable aromatic compound and the transalkylating agent is the same compound, for example, when toluene serves as the donor and acceptor of a transferred methyl group to produce benzene and xylene. Use of the term transalkylation includes the special case of disproportionation.

In general, the process for conversion of aromatics is conducted at conversion conditions including a temperature of from about 200° C. to about 760° C., a pressure of from about atmospheric (bar) to about 200 atmospheres, a weight hourly space velocity of from about 0.08 hr$^{-1}$ to about 2000 hr$^{-1}$ and a hydrogen/feedstock hydrocarbon compound mole ratio of from 0 (no added hydrogen) to about 100.

Such aromatic conversion processes include, as non-limiting examples, isomerizing xylene feedstock components to product enriched in p-xylene with reaction condition including a temperature from about 230° C. to about 510° C., a pressure of from about 3 atmospheres to about 35 atmospheres, a weight hourly space velocity of from about 0.1 hr$^{-1}$ to about 200 hr$^{-1}$ and a hydrogen/hydrocarbon mole ratio of from about 0 to about 100; disproportionating toluene to product comprising benzene and xylenes with reaction conditions including a temperature of from about 200° C. to about 760° C., a pressure of from about atmospheric to about 60 atmospheres and a weight hourly space velocity of from about 0.08 hr$^{-1}$ to about 20 hr$^{-1}$; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 300° C. to about 500° C., a pressure of from about atmospheric to about 200 atmospheres, a weight hourly space velocity of from about 2 hr$^{-1}$ to about 2000 hr$^{-1}$ and a feedstock aromatic hydrocarbon/alkylating agent mole ratio of from about 1/1 to about 20/1; and transalkylating aromatic hydrocarbons in the presence of polyalkylaromatic hydrocarbons with reaction aonditions including a temperature of from about 340° C. to about 500° C., a pressure of from about atmospheric to about 200 atmospheres, a weight hourly space velocity of from about 10 hr$^{-1}$ to about 1000 hr$^{-1}$ and a feedstock aromatic hydrocarbon/polyalkylaromatic hydrocarbon mole ratio of from about 1/1 to about 16/1.

As is known in the art, ZSM-5 type zeolitic materials are members of a novel class of zeolites that exhibit unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The preferred zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although in some instances excessive puckering of the rings or pore blockage may render these zeolites ineffective. 12-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index", or C.I., as herein defined may be made by passing continuously a mixture of an equal weight of normal hexane and 3-methylpentane over a small sample, approximately one gram or less, of zeolite at atmospheric pressure according to the following porcedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The C.I. is calculated as follows:

$$C.I. = \frac{\log_{10} \text{(fraction of n-hexane remaining)}}{\log_{10} \text{(fraction of 3-methylpentane remaining)}}$$

The Constraint Index approximates the ratio of the cracking rate constants for the two hydrocarbons. Zeolites suitable for the present invention are those having a Constraint Index of 1 to 12. C.I. values for some typical zeolites are:

| CAS | C.I. |
| --- | --- |
| ZSM-4 | 0.5 |
| ZSM-5 | 6–8.3 |
| ZSM-11 | 6–8.7 |
| ZSM-12 | 2 |

| CAS | C.I. |
|---|---|
| ZSM-23 | 9.1 |
| ZSM-35 | 4.5 |
| ZSM-38 | 2 |
| TMA Offretite | 3.7 |
| Beta | 0.6–1.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth here-inabove and found to have a Constraint Index of 1 to 12 is intended to be included in the instant catalyst definition regardless that the same identical zeolite tested under other defined conditions may give a Constraint Index value outside of 1 to 12.

The class of zeolites defined herein as "ZSM-5 type" is exemplified by those having the structures of ZSM-5, ZSM-11, ZSM-12, ZSM-23, ZSM-35, ZSM-38, ZSM-48, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particulary described in U.S. Pat. No. 4,046,859, the entire content of which is incorporated herein by reference.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites are those having the structure of ZSM-5, ZSM-11, ZSM-12, ZSM-23, ZSM-35, ZSM-38 or ZSM-48, with ZSM-5 and ZSM-11 particularly preferred. In some instances, it is advantageous to steam the fresh zeolite to reduce its activity and thereby improve its selectivity prior to use. Such improvement has been noted with steamed ZSM-5.

In a preferred aspect of this invention, the zeolites selected are those having a crystal framework density, in the dry hydrogen form, of not less than about 1.6 grams per cubic centimeter. It has been found that zeolites which satisfy all three of these criteria are most desired. Therefore, the preferred zeolites of this invention are those having a Constraint Index as defined above of about 1 to 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent not sorbed by the crystal. Or, the crystal density may be determined by mercury porosimetry, since mercury will fill the interstices between crystal but will not penetrate the intracrystalline free space. It is possible that the unusual sustained activity and stability of this class of zeolites is associated with its high crystal anionic framework density of not less that about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, 11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4, Omega | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the ZSM-5 type zeolite before treatment with $BF_3$ is conveniently converted to the hydrogen form, generally by intermediate formation of the ammonium form as a result of ammonium ion exchange and calcination of the ammonium form to yield the hydrogen form, i.e. HZSM-5. In addition to the hydrogen form, other forms of the zeolite wherein the original alkali metal has been reduced to less than about 1.5 percent by weight may be used.

In practicing the desired conversion process, it may be desirable to incorporate the above-described crystalline aluminosilicate in another matrix resistant to temperature and other conditions employed in the process. However, it has been found that such incorporation preferably should not take place until after the zeolite has been treated with boron trifluoride since the presence of some matrices, for reasons which are not completely understood, interferes with the activation procedure. This is particularly true for alumina (or alumina-containing) matrices. Silica matrices may not be detrimental to the activation procedure and could be composited with the zeolite prior to activation with boron trifluoride.

The modified zeolite, if treated with $BF_3$ in the absence of binder, may be incorporated with any conventional matrix material. Such matrix materials include synthetic or naturally occuring substances as well as inorganic materials such as clay, silica and/or metal oxides. Natural clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

Although there is generally some type of correlation between alpha value and catalytic activity in the conversions contemplated in this invention, the alpha activity of the boron trifluoride treated catalyst was much reduced by the treatment, but the conversion of methanol went up (Table 1). This is a surprising and unexpected result which is not understood.

The following examples will illustrate the best mode contemplated for carrying out the invention.

EXAMPLE 1

A sample of HZSM-5 having a silica-to-alumina ratio of 70:1 and without binder was treated with boron trifluoride by contacting it at 150° C. and at atmospheric pressure with boron trifluoride flowing at 30 cc/min. through a 1 gram catalyst bed for approximately 10 minutes, after which the zeolite was cooled in a steam of dry nitrogen.

EXAMPLES 2-6

The boron trifluoride modified catalyst of Example 1 was then tested for conversion of methanol to hydrocarbons along with an HZSM-5 type zeolite which had not been boron trifluoride modified. The following Table 1 compares data from the catalyst of this invention with the catalyst of the prior art.

TABLE 1

| Example | Catalyst | Temp, °C. | WHSV | Conversion wt. % | Approximate WHSV to Achieve 100% Conv. | Approximate Activity Enhancement Factor |
| --- | --- | --- | --- | --- | --- | --- |
| 2 | HZSM-5 | 300 | 1.2 | 46 | 0.6 | — |
| 3 | HZSM-5 | 300 | 1.5 | 35 | 0.5 | — |
| 4 | HZSM-5 | 300 | 6.2 | 7 | 0.5 | — |
| 5 | $BF_3$ HZSM-5 | 300 | 9.0 | 100 | 9.0 | 15-20 |
| 6 | $BF_3$ HZSM-5 | 280 | 2.3 | 100 | 2.3 | 4-5 |

As can be seen from the above table, a space velocity of approximately 0.5 is required to achieve 100% methanol conversion at 300° C. for an untreated HZSM-5. For the boron trifluoride modified catalyst, a space velocity of 9.0 achieves 100% methanol conversion. This corresponds to an increase in catalyst activity by a factor of approximately 15-20. Even at 280° C., the $BF_3$ modified catalyst is four to five times as active as the unmodified catalyst at 300° C.

EXAMPLES 7-13

A series of experiments were carried out in order to demonstrate the uniqueness of the novel activation procedure of this invention.

In each of Examples 7-13, HZSM-5 having a silica-to-alumina ratio of 70:1 was employed. In Examples 7 and 10, the conventional HZSM-5 catalyst of the prior art was employed. In Examples 8 and 11, and HZSM-5 treated with boron fluoride in the manner set forth in Examples 2-6 was employed.

In Example 9, an ammonium fluoride treated catalyst was employed. This catalyst was prepared by mixing 0.46 gram of ammonium fluoride with 1.0 gram of HZSM-5 (no binder) and heating at 150° C. for 10 minutes with argon flowing at 30 cc/min. These conditions simulate those used for the preparation of $BF_3$ catalyst. The catalyst of Example 9 was then calcined in air at 500° C. overnight to convert it to the hydrogen form. In Example 12, a mixture of HZSM-5 with alumina was treated with $BF_3$ in the manner previously described. In Example 13, a hydrogen fluoride treated catalyst was used. This catalyst was prepared by flowing a mixture of 3 cc of hydrogen fluoride and 27 cc of argon at 300 cc/min. over 1 gram of HZSM-5 (no binder) at 150° C. for 15 minutes. The results obtained for methanol conversion as well as alpha values of the various catalyst are given in Table 2.

TABLE 2

Conversion of Methanol Over ZSM-5 Catalysts
SiO$_2$/Al$_2$O$_3$ = 70/1

| Example | Catalyst | Alpha | Temp, °C. | WHSV | Conversion wt. % | Approximate WHSV for 100% Conv. | Approximate Activity Enhancement Factor |
|---|---|---|---|---|---|---|---|
| 7 | HZSM-5 | 150 | 280 | 2.3 | 32 | 0.7 | — |
| 8 | BF$_3$—HZSM-5 | 10 | 280 | 4.5 | 64 | 2.9 | 4.1 |
| 9 | NH$_4$F Treated HZSM-5 | 150 | 280 | 2.0 | 34 | 0.7 | 1.0(a) |
| 10 | HZSM-5 | 150 | 300 | 9.0 | 14 | 1.2 | — |
| 11 | BF$_3$—HZSM-5 | 0 | 300 | 6.0 | 58 | 3.5 | 2.9 |
| 12 | BF$_3$—HZSM-5 Binder | 6 | 300 | 2.0 | 83 | 1.7 | 1.4 |
| 13 | HF Treated HZSM-5 | 18 | 300 | 2.0 | 10 | 0.2 | 0.2(b) |

(a) No activation relative to parent HZSM-5
(b) Deactivated relative to parent HZSM-5

As can be seen from the above table, the catalyst of Example 8 had a substantially lower alpha activity than the catalyst of Example 7, yet it had enhanced activity for the conversion of methanol. The same is equally true with regard to the catalyst of Example 11 as compared to the catalyst of Example 10. Please note that treatment with ammonium fluoride, i.e. Example 9, and hydrogen fluoride, i.e. Example 13 did not result in enhancement of methanol conversion activity and, in fact, Example 13 shows an actual decline relative to the untreated material.

Example 12 depicts the results of incorporating an HZSM-5 into an alumina binder prior to treatment with boron trifluoride and, as can be seen, a catalyst was obtained with an alpha of 6 and only slightly enhanced activity at 300° C. The BF$_3$ appears to react much more rapidly with the alumina binder than with the ZSM-5.

EXAMPLES 14–17

These examples will illustrate the criticality of the silica-to-alumina ratio of the ZSM-5 type zeolite. In Examples 14 and 15, a crystalline ZSM-5 zeolite having a silica-to-alumina ratio of 800:1 was employed. In Examples 16 and 17, a similar material but having a silica-to-alumina ratio of 1600:1 was employed. The method of activation with boron trifluoride was the same as previously described. The results are shown in Table 3.

TABLE 3

Conversion of Methanol Over ZSM-5 Catalysts

| Example | Catalyst | Alpha | Temp, °C. | WHSV | Conversion wt. % | Approximate WHSV for 100% Conv. | Approximate Activity Enhancement Factor |
|---|---|---|---|---|---|---|---|
| 14 | HZSM-5(a) BF$_3$— | 14 | 340 | 4.0 | 76 | 3.0 | — |
| 15 | HZSM-5(a) | 0.5 | 340 | 4.0 | 56 | 2.2 | 0.7 |
| 16 | HZSM-5(b) BF$_3$ | 7 | 400 | 10 | 13 | 1.3 | — |
| 17 | HZSM-5(b) | 1.6 | 390 | 2.0 | 54 | 1.1 | 0.8 |

(a) SiO$_2$/Al$_2$O$_3$ = 800/1
(b) SiO$_2$/Al$_2$O$_3$ = 1600/1

As can be seen from the table, treatment with boron trifluoride did not enhance the methanol conversion activity of either of these two ZSM-5's simply because the silica-to-alumina ratio was too high.

Therefore, the novel process of this invention is applicable to ZSM-5 type zeolites having a silica-to-alumina ratio of from about 30 to no greater than about 300 and, more preferably, no greater than about 100 and, even more desirably, having a silica-to-alumina ratio of from about 30 to about 80.

EXAMPLE 18

A boron trifluoride modified catalyst prepared as in Example 1 was tested for propylene conversion (oligomerization) at 300° C. and 30 WHSV. Table 4 compares the data obtained with the boron trifluoride modified catalyst with data obtained using HZSM-5 of similar activity (alpha-test) at the same operation conditions.

As can be seen from Table 4, propylene conversion was approximately 16 times higher for the boron trifluoride treated catalyst compared to untreated HZSM-5. In addition, the boron trifluoride treated catalysts produced more of desirable C$_6$+ gasoline range hydrocarbons. Other olefins would be expected to react similarly to propylene.

TABLE 4

| | BF$_3$—HZSM-5 | HZSM-5 |
|---|---|---|
| Temperature, °C. | 300 | 300 |
| WHSV | 30 | 30 |
| Catalyst Activity, ($\alpha$) | 0.14 | 0.16 |
| Conversion, wt % | 99 | 6 |
| Product distribution, wt % | | |
| Methane | 0.0 | 0.0 |
| Ethane | 0.0 | 0.0 |
| Ethylene | 0.2 | 0.0 |
| Propane | 3.3 | 1.0 |
| Propylene | — | — |
| i-Butane | 6.9 | 2.9 |
| n-Butane | 3.1 | 2.0 |
| C$_4$ Olefins | 11.3 | 17.0 |
| C$_5$ Olefins | 3.6 | 15.5 |
| C$_6$ Olefins | 13.8 | 30.2 |
| C$_7$ Olefins | 10.5 | 10.4 |
| C$_8$ Olefins | 33.4 | 8.4 |
| C$_9$ Olefins | 11.5 | 12.4 |
| C$_{10}$ Olefins | 2.3 | 0.2 |

TABLE 4-continued

| | BF$_3$—HZSM-5 | HZSM-5 |
|---|---|---|
| | 99.9 | 100.0 |

EXAMPLE 19

A boron trifluoride catalyst prepared as in Example 1 was tested for toluene disproportionation at 500° C. and 10 WHSV. Table 2 summarizes the data and compares them with data obtained using HZSM-5 of similar activity (alpha-test).

As can be seen from Table 5, at the same operating conditions and using catalysts of the same alpha-activity, the boron trifluoride catalyst showed approximately 18 times higher conversion compared to untreated HZSM-5.

TABLE 5

| | BF$_3$—HZSM-5 | HZSM-5 |
|---|---|---|
| Temperature, °C. | 500 | 500 |
| WHSV | 10 | 10 |
| Catalyst Activity (alpha-test) | 2.2 | 2.2 |
| Conversion, wt % | 5.07 | 0.28 |

EXAMPLE 20

A boron trifluoride catalyst prepared as in Example 1 was tested for xylene isomerization at 10 WHSV and various temperatures. Table 6 summarizes the data and compares them with data obtained using HZSM-5 of similar activity (alpha-test).

As can be seen from Table 6, at 300° C. and using catalysts of the same alpha-activity, the boron trifluoride catalyst showed approximately four times higher conversion compared to untreated HZSM-5. In order to obtain equivalent conversions, the temperature of the boron trifluoride catalyst had to be significantly lowered to 230° C.

TABLE 6

| | BF$_3$—HZSM-5 | | HZSM-5 |
|---|---|---|---|
| Temperature, °C. | 300 | 230 | 300 |
| WHSV | 10 | 10 | 10 |
| Catalyst Activity (alpha-test) | 2.2 | 2.2 | 2.2 |
| Conversion, wt. % | 16.3 | 4.3 | 4.6 |

EXAMPLE 21

Several preparations were made by the method used in Example 1 and were evaluated for physical properties, including selectivity for ethylene produced when converting methanol at 100% conversion. The results are summarized in Table 7.

TABLE 7

| Physical Property | HZSM-5 | Range for BF$_3$—HZSM-5 |
|---|---|---|
| Alpha Value | 150 (typical) | 0 to 29 |
| Crystallinity, % | 100 | 90 to 95 |
| O—xylene sorption Capacity, mg/g | 50 | 19 |
| Diffusion time for 30% of capacity for O-xylene, minutes | 270 | 900 |
| Wt % Boron | 0 | 0.1–0.5 |
| Wt % Fluorine | 0 | 5 to 10 |
| Ethylene selectivity, 100% Methanol Conversion, wt % | 8 | 18 |

Although this invention is described particularly with reference to BF$_3$, it is contemplated to employ other Lewis acid fluorides such as PF$_3$, AsF$_3$, SbF$_5$ and BiF$_5$ in place of BF$_3$.

What is claimed is:

1. A process for converting feedstock comprising C$_2$+ olefins to oligomerization conversion product comprising up to about 99.9 wt. % non-aromatics, up to about 96.4 wt. % total C$_4$+ aliphatics and olefins and up to about 71.5 wt. % C$_6$–C$_{10}$ olefins which comprises contacting said feedstock at conversion conditions suitable to convert said feedstock to said product with a catalyst composition comprising a crystalline zeolite having been modified by the method comprising contacting said zeolite having a silica-to-alumina mole ratio of from about 30 to about 300 and a Constraint Index of from about 1 to about 12 with gaseous boron trifluoride in the absence of binder and under a combination of conditions of temperature, contact time and pressure, said combination of conditions being effective to reduce the activity of the zeolite for cracking normal hexane as measured by the alpha test conducted at 538° C.

2. The process of claim 1 wherein said gaseous boron trifluoride contacting is conducted at a temperature of from about 25° C. to about 500° C. and a pressure of from about 0.01 psig to about 500 psig for a time of from about 0.01 hour to about 10 hours.

3. The process of claim 1 wherein said gaseous boron trifluoride contacted zeolite is purged with an inert gas.

4. The process of claim 2 wherein said gaseous boron trifluoride contacted zeolite is purged with an inert gas.

5. The process of claim 1 wherein said zeolite has the structure of ZSM-5, ZSM-11, ZSM-12, ZSM-23, ZSM-35, ZSM-38 or ZSM-48.

6. The process of claim 1 wherein said zeolite is in the acid form.

7. The process of claim 5 wherein said zeolite is in the acid form.

8. The process of claim 5 wherein said zeolite has the structure of ZSM-5.

9. The process of claim 1 wherein said conversion conditions include a temperature of from about 100° C. to about 700° C., a pressure of from about 10 kPA to about 11,000 kPa, a liquid hourly space velocity of from about 0.1 hr$^{-1}$ to about 500 hr$^{-1}$ and a hydrogen/hydrocarbon mole ratio of from 0 to about 20.

10. The process of claim 1 wherein said feedstock comprises propylene.

11. A process for converting feedstock comprising C$_2$–C$_7$ olefins to conversion product comprising non-aromatic gasoline components including C$_6$+ olefins which comprises contacting said feedstock at conversion conditions sufficient to convert said feedstock to said product with a catalyst composition comprising a crystalline zeolite having been modified by the method comprising contacting said zeolite having a silica-to-alumina mole ratio of from about 30 to about 300 and a Constraint Index of from about 1 to about 12 with gaseous boron trifluoride in the absence of binder and under a combination of conditions of temperature, contact time and pressure, said combination of conditions being effective to reduce the activity of the zeolite for cracking normal hexane as measured by the alpha test conducted at 538° C.

12. The process of claim 11 wherein said conversion conditions include a temperature of from about 190° C. to about 375° C., a pressure of from about 400 kPa to about 11,000 kPa and a liquid hourly space velocity of from about 0.3 hr$^{-1}$ to about 2 hr$^{-1}$.

13. The process of claim 12 wherein said conversion conditions include a temperature of from about 190° C. to about 315° C., a pressure of from about 4200 kPa to about 11,000 kPa and a liquid hourly space velocity of from about 0.3 hr$^{-1}$ to about 1 hr$^{-1}$.

14. The process of claim 12 wherein said conversion conditions include a temperature of from about 230° C. to about 375° C., a pressure of from about 400 kPa to about 4700 kPa and a liquid hourly space velocity of from about 0.3hr$^{-1}$ to about 2hr$^{-1}$.

15. The process of claim 11 wherein said feedstock comprises propylene.

16. A process for converting feedstock comprising $C_2{}^+$ olefins to oligomerization conversion product comprising up to about 99.9 wt. % non-aromatics, up to about 96.4 wt. % total $C_4{}^+$ aliphatics and olefins and up to about 71.5 wt. % $C_6$-$C_{10}$ olefins which comprises contacting said feedstock at conversion conditions suitable to convert said feedstock to said product with a catalyst composition comprising a crystalline material having been modified by the method comprising contacting said crystalline material having a silica-to-alumina ratio of from about 30 to about 300 and the structure of ZSM-5 with gaseous boron trifluoride in the absence of binder and under a combination of conditions of temperature, contact time and pressure, said combination of conditions being effective to reduce the activity of the crystalline material for cracking normal hexane as measured by the alpha test conducted at 538° C.

17. The process of claim 15 wherein said feedstock comprises propylene.

* * * * *